(12) United States Patent
Zhuang

(10) Patent No.: US 12,739,552 B1
(45) Date of Patent: Sep. 15, 2026

(54) FLEXIBLE SLEEPING HEADBAND-TYPE SPEAKER

(71) Applicant: Shaogeng Zhuang, Jieyang (CN)

(72) Inventor: Shaogeng Zhuang, Jieyang (CN)

( * ) Notice: Subject to any disclaimer, the term of this patent is extended or adjusted under 35 U.S.C. 154(b) by 0 days.

(21) Appl. No.: 19/641,733

(22) Filed: Apr. 8, 2026

(51) Int. Cl.
*H04R 1/10* (2026.01)
*A61F 9/04* (2006.01)
*H04R 1/02* (2006.01)

(52) U.S. Cl.
CPC ............ *H04R 1/1008* (2013.01); *A61F 9/04* (2013.01); *H04R 1/028* (2013.01); *H04R 1/105* (2013.01); *H04R 1/1083* (2013.01); *A61F 2210/0057* (2013.01); *A61F 2250/0007* (2013.01)

(58) Field of Classification Search
None
See application file for complete search history.

(56) References Cited

U.S. PATENT DOCUMENTS 11,622,889 B1 * 4/2023 Li ......................... A61M 21/02 381/301
2019/0149903 A1 * 5/2019 Dowding-Young ...... A61F 9/04 381/74
2021/0375253 A1 * 12/2021 Turner-Fernback ........................ H04R 1/1083

* cited by examiner

*Primary Examiner* — Antim G Shah
(74) *Attorney, Agent, or Firm* — HOWARD M COHN and Associates, LLC

(57) ABSTRACT

A flexible sleeping headband-type speaker includes an annular headband, two sound-producing bodies, and cushioning layers. The annular headband includes an adjustable segment, an eye-mask segment, and ear-covering segments. The adjustable segment is disposed along a circumference of the annular headband to adjust a perimeter of the annular headband. The ear-covering segments are symmetrically disposed and are respectively configured to cover a left ear and a right ear. Each of the ear-covering segments features at least a dual-layer structure consisting of an inner layer and an outer layer. Each of the sound-producing bodies is a flat structure. Each of the sound-producing bodies is positioned between the inner layer and the outer layer of a corresponding one of the ear-covering segments. The cushioning layers are configured to disperse and alleviate any localized pressure that the sound-producing bodies exert on the left ear and the right ear.

14 Claims, 11 Drawing Sheets

FLEXIBLE SLEEPING HEADBAND-TYPE SPEAKER

TECHNICAL FIELD

The present disclosure relates to a technical field of sound-producing bodies, and in particular to a flexible sleeping headband-type speaker.

BACKGROUND

In an audio sleeping eye mask in the related art, miniature speaker units thereof are directly disposed in paddings on two sides of an eye mask body thereof, thereby forming an integrated structure for physical light-blocking and audio playback. The audio sleeping eye mask aims to achieve a convenient experience of blocking light and transmitting sound through structural integration, without the need for wearing additional headphones.

However, the miniature speaker units of such audio sleeping eye masks commonly lack flexible cushioning structures. After prolonged wearing, auricles of the user are prone to pain due to rigid pressure exerted by the miniature speaker units.

SUMMARY

To address a problem that existing audio sleeping eye masks lack flexible cushioning structures for headphones thereof, causing ear pain due to hard pressure of the headphones, the present disclosure provides a soft headband speaker suitable for use while falling asleep.

The flexible sleeping headband-type speaker comprises an annular headband, two sound-producing bodies, and cushioning layers. The annular headband comprises an adjustable segment, an eye-mask segment and ear-covering segments. The adjustable segment is disposed along a circumference of the annular headband to adjust a perimeter of the annular headband, so as to adapt to different head sizes while maintaining a gentle tension. The eye-mask segment is configured to cover an eye area, and a width of the eye-mask is sufficient to provide a light-blocking function. The ear-covering segments are symmetrically disposed and are respectively configured to cover a left ear and a right ear. A width of each of the ear-covering segments is sufficient to provide a noise-muffling effect. Each of the ear-covering segments features at least a dual-layer structure consisting of an inner layer and an outer layer.

Each of the sound-producing bodies is a flat structure. The sound-producing bodies are configured to receive audio information and convert the audio information into audio sound waves. Each of the sound-producing bodies is positioned between the inner layer and the outer layer of a corresponding one of the ear-covering segments. An acoustic axis of each of the sound-producing bodies is roughly perpendicular to the corresponding one of the ear-covering segments and faces inward. The cushioning layers are made of a sound-permeable material, each of the cushioning layers is positioned between the inner layer of a corresponding one of the ear-covering segments and a corresponding one of the sound-producing bodies. The cushioning layers are configured to disperse and alleviate any localized pressure that the sound-producing bodies exert on the left ear and the right ear.

Optionally, each of the cushioning layers and the outer layer of the corresponding one of the ear-covering segments are sewn to form a U-shaped pocket that is horizontally disposed. Each U-shaped pocket is configured to accommodate a corresponding one of the sound-producing bodies. A sound emitted by each of the sound-producing bodies is capable of passing through a corresponding one of the cushioning layer and the inner layer of the corresponding one of the ear-covering segments to reach a corresponding ear.

Optionally, each of the cushioning layers and the inner layer of the corresponding one of the ear-covering segments are sewn together to form a closed interlayer, so that each of the sound-producing bodies is prevented from being mistakenly placed between each of the cushioning layers and the inner layer of the corresponding one of the ear-covering segments Optionally, a pocket opening of each U-shaped pocket is located between each U-shaped pocket and the eye-mask segment, so that each of the sound-producing bodies is allowed to be placed into a corresponding U-shaped pocket from front to rear.

Optionally, the pocket opening of each U-shaped pocket is disposed on an inner side of the annular headband to avoid affecting an appearance of the annular headband.

Optionally, in a transition area between each of the ear-covering segments and the eye-mask segment, the inner layer of each of the ear-covering segments is sewn onto an inner layer of the eye-mask segment. An upper part of a sewn line thereof defines a pick-and-place gap having a size not less than a width of each of the sound-producing bodies, so as to form each pocket opening.

Optionally, the pick-and-place gap of each pocket opening is perpendicular to the circumference of the annular headband, so that an opening direction of the pocket opening faces toward the eye-mask segment along the circumference of the annular headband.

Optionally, an edge of the pocket opening of the inner layer of each of the ear-covering segments is sewn with a pocket binding. Each pocket binding is inwardly-folded. Each pocket binding is tubular and hollow. A reinforcing rib is wrapped by each pocket binding to prevent excessive deformation of each pocket opening, so as to reduce pulling of each pocket opening when placing or removing a corresponding one of the sound-producing bodies and avoid premature damage to each U-shaped pocket.

Optionally, an internal width of each U-shaped pocket is greater than a width of each pocket opening, so as to prevent each of the sound-producing bodies from sliding out of a corresponding pocket opening during a non-operational state.

Optionally, an internal depth of each U-shaped pocket is greater than a length of each of the sound-producing bodies, so as to facilitate a user to adjust a longitudinal position of each of the sound-producing bodies within the corresponding one of the ear-covering segments to accommodate different users.

Optionally, a noise-muffling effect of a material of the inner layer of each of the ear-covering segments is less than a noise-muffling effect of a material of the outer layer of each of the ear-covering segments, so as to reduce attenuation of a volume of each of the sound-producing bodies.

Optionally, the cushioning layers are made of a fluffy cotton material. Each of the ear-covering segments further comprises a middle layer covering a corresponding one of the cushioning layers. Each middle layer is disposed between the corresponding one of the cushioning layers and a corresponding one of the sound-producing bodies. For each of the ear-covering segments, the middle layer thereof, the corresponding one of the cotton product, and the inner layer thereof are sequentially overlapped and sewn to form a closed interlayer, and a space between the outer layer thereof and the middle layer thereof is sewn to form a non-closed interlayer. Each non-closed interlayer is defined as each U-shaped pocket.

Optionally, two ends of the adjustable segment are respectively sewn to tail portions of the ear-covering segments away from the eye-mask segment to form the annular headband, so as to adjust the perimeter of the annular headband.

Optionally, the adjustable segment of the annular headband is made of an elastic fabric; or the adjustable segment of the annular headband is formed by two segments attached via hook-and-loop fasteners; or the adjustable segment of the annular headband is formed by two segments hooked via buckles; or the adjustable segment of the annular headband is formed by two segments pressed via snap buttons.

Optionally, the width of the eye-mask segment is greater than the width of each of the ear-covering segments. The width of each of the ear-covering segments is greater than a width of the adjustable segment. The annular headband features a stepwise decreasing width that is wider at a front portion thereof and narrower at a rear portion thereof.

Optionally, a length of the eye-mask segment distributed along the circumference of the annular headband is less than a sum of lengths of the two ear-covering segments and a length of the adjustable segment.

Optionally, in a packaging state of the flexible sleeping headband-type speaker, the eye-mask segment is folded inward from a middle portion thereof to substantially wrap the ear-covering segments and the adjustable segment inside the eye-mask segment. An area of each pocket opening facing away from the ear-covering segments is configured as an inwardly-folded position. A middle portion of the adjustable segment is configured as an outwardly-folded position. A packaging thickness of the flexible sleeping headband-type speaker is approximately twice a thickness of the eye-mask segment plus a total thickness of the ear-covering segments.

The present disclosure further provides a flexible sleeping headband-type speaker. The flexible sleeping headband-type speaker comprises an annular headband, two sound-producing bodies, and a control system. The annular headband comprises an adjustable segment, an eye-mask segment, and ear-covering segments. The adjustable segment is disposed along a circumference of the annular headband to adjust a perimeter of the annular headband, so as to adapt to different head sizes while maintaining a gentle tension. The eye-mask segment is configured to cover an eye area. The ear-covering segments are symmetrically disposed and are respectively configured to cover a left ear and a right ear. Each of the ear-covering segments features at least a triple-layer consisting of an inner layer, and an outer layer, and a cushioning layer disposed between the inner layer and the outer layer. Each of the sound-producing bodies is a flat structure. The sound-producing bodies are configured to receive audio information and convert the audio information into audio sound waves. Each of the sound-producing bodies is positioned between the cushioning layer and the outer layer of a corresponding one of the ear-covering segments. An acoustic axis of each of the sound-producing bodies is roughly perpendicular to the corresponding one of the ear-covering segments. A sound emitted by each of the sound-producing bodies is capable of passing through the cushioning layer and the inner layer of the corresponding one of the ear-covering segments to reach a corresponding ear.

The control system is configured to control the sound-producing bodies and is disposed on a middle portion of the eye-mask segment. A circuit board of the control system is fixed in an interlayer of the eye-mask segment. A control panel of the control system is fixed on an outer surface of the eye-mask segment, and connecting wires connecting the control system and the sound-producing bodies pass through an interlayer of the annular headband.

Optionally, each cushioning layer is made of a sound-permeable material to disperse and alleviate localized pressure that each of the sound-producing bodies exerts on a corresponding ear. For each of the ear-covering segments, the cushioning layer thereof and the inner layer thereof are sewn to form a closed interlayer, and the cushioning layer thereof and the outer layer thereof are sewn to form a U-shaped pocket configured to accommodate a corresponding one of the sound-producing bodies.

The present disclosure further provides a flexible sleeping headband-type speaker. The flexible sleeping headband-type speaker comprises an annular headband, two sound-producing bodies, and a charging case. The annular headband comprises an adjustable segment, an eye-mask segment, and ear-covering segments. The adjustable segment is disposed along a circumference of the annular headband to adjust a perimeter of the annular headband, so as to adapt to different head sizes while maintaining a gentle tension. The eye-mask segment is configured to cover an eye area.

The ear-covering segments are symmetrically disposed and are respectively configured to cover a left ear and a right ear. Each of the ear-covering segments features at least a triple-layer consisting of an inner layer, and an outer layer, and a cushioning layer disposed between the inner layer and the outer layer. Each cushioning layer is made of a sound-permeable material to disperse and alleviate localized pressure that each of the sound-producing bodies exerts on a corresponding ear. Each of the sound-producing bodies is a flat structure. Each of the sound-producing bodies is positioned between the cushioning layer and the outer layer of a corresponding one of the ear-covering segments. A sound emitted by each of the sound-producing bodies is capable of passing through the cushioning layer and the inner layer of the corresponding one of the covering segments to reach a corresponding ear. The sound-producing bodies are allowed to be charged in the charging case after being taken out of the annular headband.

In the flexible sleeping headband-type speaker, each cushioning layer made of a sound-permeable material is disposed between each of the sound-producing bodies and the corresponding ear of the user. Each cushioning layer acts as a buffering pad to absorb a concentrated pressure generated by a rigid shell of each of the sound-producing bodies and disperse concentrated pressure over a larger contact surface of the corresponding ear. The flat structure of each of the sound-producing bodies minimizes thickness to adapt to a limited space within a corresponding interlayer of annular headband while increasing a pressure-bearing area to avoid excessive local pressure. In this way, it ensures that while the user enjoys music, the auricles are no longer subjected to a rigid pressure from each of the sound-producing bodies, which fundamentally resolves an issue where "earphones of existing audio sleeping eye masks lack flexible buffering structures, leading to auricular pain after prolonged wearing", thereby facilitating long-term wearing of the sound-producing bodies during sleep without interfering with rest due to discomfort.

BRIEF DESCRIPTION OF DRAWINGS

In order to clearly describe technical solutions in the embodiments of the present disclosure, the following will briefly introduce the drawings that need to be used in the description of the embodiments or the prior art. Apparently, the drawings in the following description are merely some of the embodiments of the present disclosure, and those skilled in the art are able to obtain other drawings according to the drawings without contributing any inventive labor.

Figure 1:
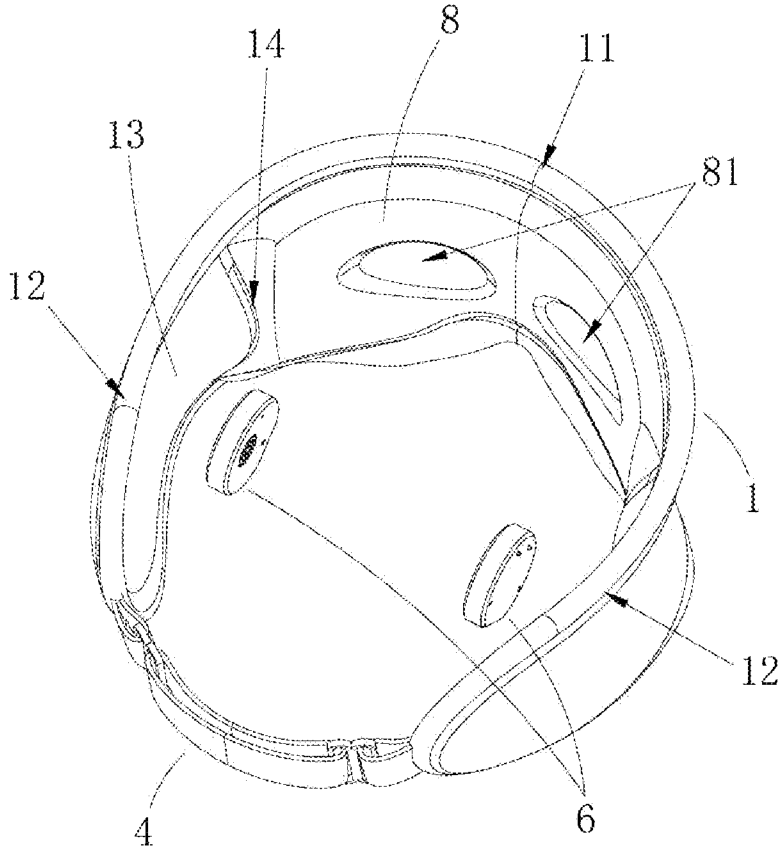
FIG. 1 is an exploded schematic diagram of an annular headband and sound-producing bodies of the present disclosure.
Figure 2:
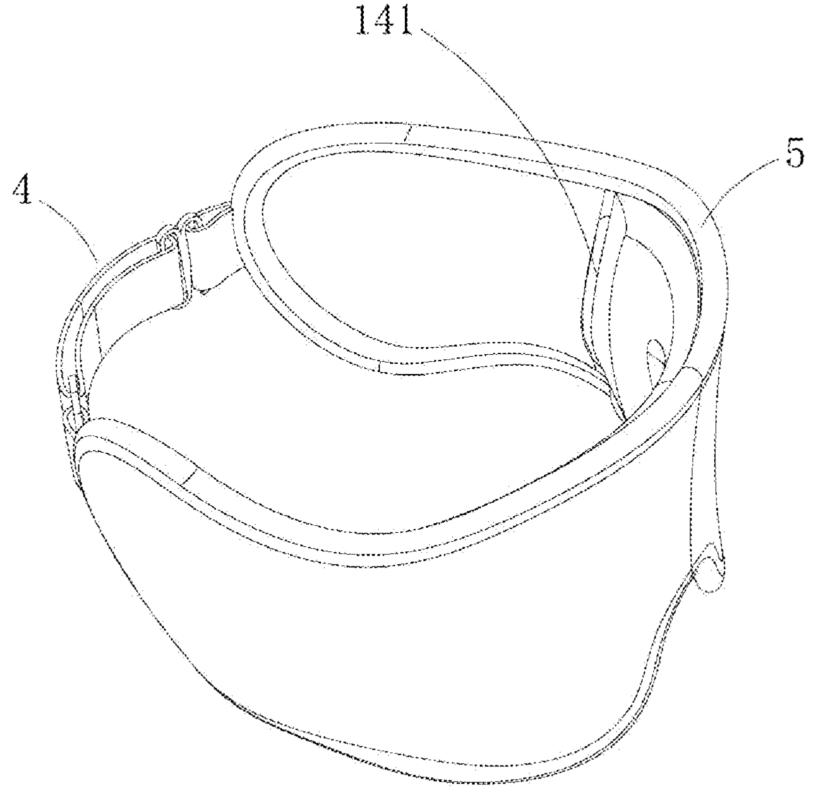
FIG. 2 is a perspective schematic diagram of the annular headband of the present disclosure.
Figure 3:
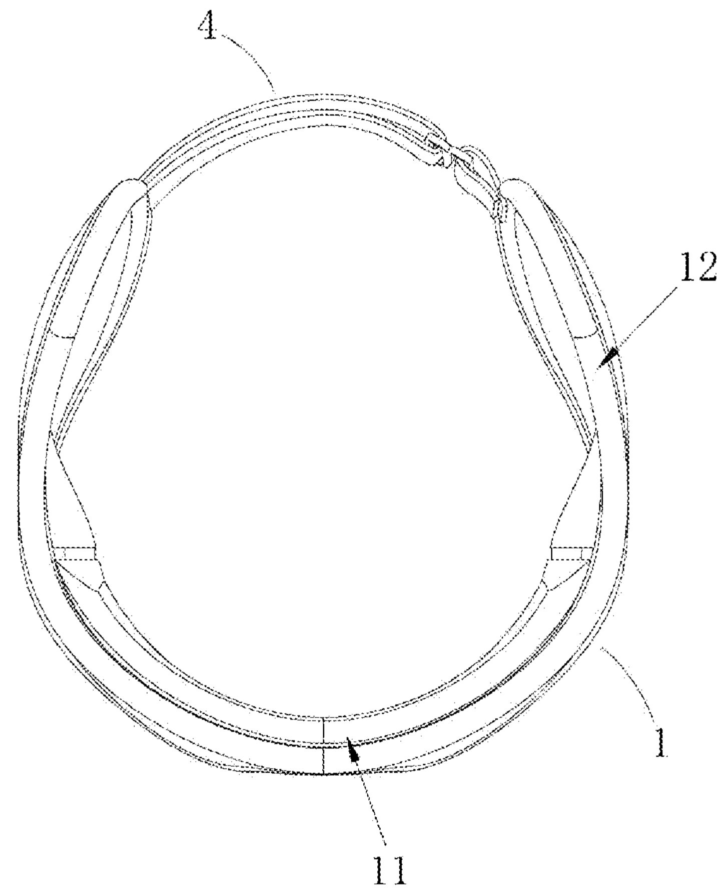
FIG. 3 is a top plan schematic diagram of the annular headband according to a first embodiment of the present disclosure.

In the drawings: 1—annular headband; 11—eye-mask segment; 12—ear-covering segment; 121—inner layer of the ear-covering segment; 122—outer layer of the ear-covering segment; 123—middle layer of the ear-covering segment; 13—U-shaped pocket; 14—pocket opening; 141—pocket binding; 15—nose-bridge notch; 16—hanging ring; 2—cushioning layer; 3—light-blocking flap; 4—adjustable segment; 41—hook; 42—adjusting strap; 43—tri-glide slide; 5—binding strip; 6—sound-producing body; 61—housing; 611—sound hole; 612—flat wall; 63—indicator light; 71—power output component; 72—charging case; 721—charging cavity; 722—finger groove; 73—flipping cover; 8—cushioning lining; 81—recess.

DETAILED DESCRIPTION

Unless otherwise defined, all technical and scientific terms used herein have the same meaning as commonly understood by those skilled in the art of the present disclosure. The terminology used in the specification is for the purpose of describing specific embodiments only and is not intended to limit the present disclosure. As used herein, the term "and/or" includes any and all combinations of one or more of the associated listed items. The terms "comprise" and "have and any variations thereof in the description and claims of the present disclosure and the above-mentioned drawings are intended to cover non-exclusive inclusion. The terms "first", "second", etc., in the specification and claims of the present disclosure or the above drawings, are used to distinguish different objects, rather than to describe a specific order.

Reference herein to "embodiment" means that a particular feature, structure, or characteristic described in connection with one embodiment may be included in at least one embodiment of the present disclosure. The appearances of the "embodiment" in various positions in the specification are not necessarily referring to the same embodiment, and are not independent or alternative embodiments mutually exclusive of other embodiments. Those skilled in the art explicitly and implicitly understand that the embodiments described herein may be combined with other embodiments.

To enable those skilled in the art to better understand the present disclosure, the technical solutions in the embodiments of the present disclosure will be clearly and completely described below with reference to the accompanying drawings.

As shown in FIGS. 1-11, the present disclosure provides a flexible sleeping headband-type speaker. The flexible sleeping headband-type speaker comprises an annular headband 1, two sound-producing bodies 6, and cushioning layers 2. The annular headband 1 comprises an adjustable segment 4, an eye-mask segment 11, and ear-covering segments 12. The adjustable segment 4 is disposed along a circumference of the annular headband 1 to adjust a perimeter of the annular headband 1, so as to adapt to different head sizes while maintaining a gentle tension. The eye-mask segment 11 is configured to cover an eye area, and a width of the eye-mask is sufficient to provide a light-blocking function. The ear-covering segments 12 are symmetrically disposed and are respectively configured to cover a left ear and a right ear. A width of each of the ear-covering segments 12 is sufficient to provide a noise-muffling effect. Each of the ear-covering segments 12 features at least a dual-layer structure consisting of an inner layer 121 and an outer layer.

Each of the sound-producing bodies 6 is a flat structure. The sound-producing bodies 6 are configured to receive audio information and convert the audio information into audio sound waves. Each of the sound-producing bodies 6 is positioned between the inner layer 121 and the outer layer of a corresponding one of the ear-covering segments 12. An acoustic axis of each of the sound-producing bodies 6 is roughly perpendicular to the corresponding one of the ear-covering segments 12 and faces inward. The cushioning layers 2 are made of a sound-permeable material, each of the cushioning layers is positioned between the inner layer 121 of a corresponding one of the ear-covering segments 12 and a corresponding one of the sound-producing bodies 6. The cushioning layers 2 are configured to disperse and alleviate any localized pressure that the sound-producing bodies 6 exert on the left ear and the right ear.

In the embodiment, a user first fits the annular headband 1 around the head and adjusts the perimeter via the adjustable segment 4 at a rear portion of the annular headband 1. Therefore, the annular headband 1 comfortably adapts to different head sizes while maintaining a uniform and gentle tension. The eye-mask segment 11 effectively blocks external light due to its sufficient width, thereby creating a dark environment. Each of the sound-producing bodies 6 disposed within the corresponding one of the ear-covering segments 12 then starts to play audio, and the sound is transmitted inward to the ears along a direction perpendicular to a surface of the annular headband 1. In the flexible sleeping headband-type speaker, each cushioning layer made of a sound-permeable material is disposed between each of the sound-producing bodies 6 and the corresponding ear of the user. Each cushioning layer acts as a buffering pad to absorb a concentrated pressure generated by a rigid shell of each of the sound-producing bodies 6 and disperse concentrated pressure over a larger contact surface of the corresponding ear. The flat structure of each of the sound-producing bodies 6 minimizes thickness to adapt to a limited space within a corresponding interlayer of annular headband 1 while increasing a pressure-bearing area to avoid excessive local pressure. In this way, it ensures that while the user enjoys music, the auricles are no longer subjected to a rigid pressure from each of the sound-producing bodies 6, which fundamentally resolves an issue where "earphones of existing audio sleeping eye masks lack flexible buffering structures, leading to auricular pain after prolonged wearing" thereby facilitating long-term wearing of the sound-producing bodies 6 during sleep without interfering with rest due to discomfort.

Specifically, edges of at least two sheet layers forming the annular headband 1 are fixedly connected by thermal pressing in addition to sewing. In terms of manufacturing processes, two edge-joining methods are provided. A sewing method makes the annular headband 1 firm and reliable, while a thermal pressing method utilizes heat and pressure to the edges of the at least two sheet layers made of fabric, enabling stitch-free or flatter seams of the annular headband 1. A thermal pressing connection between the edges of the at least two sheet layers avoids the potential friction against the skin caused by sewing threads, particularly enhancing a delicate tactile feel of areas of the annular headband 1 that are in direct contact with the skin, such as an inner side of the eye-mask segment, thereby improving texture and user experience.

In one embodiment, non-slip decorative patterns are disposed on an outer surface of the annular headband 1. The non-slip decorative patterns (such as silicone dot matrices or stripes) are formed on an outer sheet layer of the annular headband 1 by embossing, weaving, or laminating. The non-slip decorative patterns increase a friction coefficient between the outer surface of the headband and fingers, effectively improving stability when the user handles the annular headband 1.

In one embodiment, the annular headband 1 comprises first creases at junctions between the ear-covering segments 12 and the eye-mask segment 11. A second crease is disposed at a middle portion of the eye-mask segment 11. The two ear-covering segments 12 are allowed to be folded and placed on an inner side of the eye-mask segment 11 via the first creases respectively. The eye-mask segment 11 is allowed to be folded in half via the second crease. In this way, the annular headband 1 is folded for storage. Based on the creases (i.e., the first crease and the second crease), clear folding guidance is provided for the annular headband 1. During use, the annular headband 1 is folded into a compact and regular block by simply folding the ear-covering segments 12 inward and then folding the eye-mask segment 11, which greatly reduces storage space and facilitates placement of the annular headband 1 in a travel bag, a drawer, or a matching storage pouch, thereby enhancing portability.

In one embodiment, each of the cushioning layers 2 and the outer layer of the corresponding one of the ear-covering segments 12 are sewn to form a U-shaped pocket 13 that is horizontally disposed. Each U-shaped pocket 13 is configured to accommodate a corresponding one of the sound-producing bodies 6. By connecting edges of each of the cushioning layers 2 with an inner side of the outer layer 122 of the corresponding one of the ear-covering segments via sewing threads at specific edges, each U-shaped pocket space with a pocket opening defined at one side thereof is formed. Each U-shaped pocket limits further movement of a corresponding one of the sound-producing bodies 6 within the interlayer of the annular headband 1 along a place-in direction, ensuring accuracy of the acoustic axis and a wearing angle of each of the sound-producing bodies 6, while facilitating the user to pick and place each of the sound-producing bodies 6 at any time, thus enhancing flexibility and convenience of use.

In one embodiment, each of the cushioning layers 2 and the inner layer 121 of the corresponding one of the ear-covering segments 12 are sewn together to form a closed interlayer, so that each of the sound-producing bodies 6 is prevented from being mistakenly placed between each of the cushioning layers 2 and the inner layer 121 of the corresponding one of the ear-covering segments 12. All edges of each of the cushioning layers 2 and a corresponding inner layer 121 close to the skin are sewn together to form a completely closed interlayer containing only cushioning material. Each closed interlayer physically eliminates a possibility of the user mistakenly stuffing any one of the sound-producing bodies 6 into the closed interlayer, ensuring that each of the sound-producing bodies 6 is accurately placed within the corresponding U-shaped pocket 13. Thus, it is ensured that each of the cushioning layers 2 always serves as a cushioning medium between the corresponding ear and the corresponding one of the sound-producing bodies 6, thereby ensuring cushioning effect of each of the cushioning layers 2.

In one embodiment, a pocket opening 14 of each U-shaped pocket 13 is located between each U-shaped pocket 13 and a corresponding one of the eye-mask segment 11*s*, so that each of the sound-producing bodies 6 is allowed to be placed into a corresponding U-shaped pocket 13 from front to rear. Positioning each pocket opening 14 close to the eye-mask segment 11 better suits a usage scenarios of the eye-mask segment 11 (the user generally wears the annular headband when they are lying on a bed). By having each pocket opening 14 face toward a front of the user, each of the sound-producing bodies 6 always rests against a closed end of the corresponding U-shaped pocket 13 due to gravity during use, preventing each of the sound-producing bodies 6 from slipping out through the pocket opening 14 of the corresponding U-shaped pocket 13 during use.

In one embodiment, the pocket opening 14 of each U-shaped pocket 13 is disposed on an inner side of the annular headband 1 to avoid affecting an appearance of the annular headband 1. By hiding the pocket opening 14 of each U-shaped pocket 13 on the inner side of the annular headband (one side of the annular headband fitting against the face of the user), the annular headband presents a smooth appearance without any openings or gaps when viewed from an outer side of the annular headband, preserving a clean and sleek visual design. Meanwhile, by disposing on the inner side of the annular headband 1, each pocket opening 14 and each of the sound-producing bodies 6 are well protected to reduce accidental snagging with an outside environment.

In one embodiment, in a transition area between each of the ear-covering segments 12 and the eye-mask segment 11, the inner layer 121 of each of the ear-covering segments is sewn onto an inner layer of the eye-mask segment. An upper part of this sewn line leaves a pick-and-place gap having a size not less than a width of each of the sound-producing bodies 6, so as to form the pocket opening 14. By configuring an unsewn gap reserved during sewing of the inner layer of each of the ear-covering segments 12 and the eye-mask segment 11 as the pocket opening 14, a manufacturing process is simplified without a need for additional holes or complex pocket structures.

In one embodiment, the pick-and-place gap of each pocket opening 14 is perpendicular to the circumference of the annular headband 1, so that an opening direction of the pocket opening 14 faces toward the eye-mask segment 11 along the circumference of the annular headband 1.

In one embodiment, an edge of the pocket opening 14 of the inner layer 121 of each of the ear-covering segments 12 is sewn with a pocket binding 141. Each pocket binding 141 is inwardly-folded. Each pocket binding 141 is tubular and hollow. A reinforcing rib is wrapped by each pocket binding 141 to prevent excessive deformation of each pocket opening 14, so as to reduce pulling of each pocket opening 14 when placing or removing a corresponding one of the sound-producing bodies 6 and avoid premature damage to each U-shaped pocket 13. Each pocket binding 141 that is inwardly-folded wraps an edge of a corresponding U-shaped pocket 13, so that each U-shaped pocket 13 is more durable. Each reinforcing rib (such as a thin plastic or metal strip) inserted inside a corresponding pocket binding 141 provides support for a corresponding pocket opening 14, preventing the corresponding pocket opening 14 from being excessively stretched or torn during pick-and-place operations, significantly improving a structural strength of the corresponding pocket opening 14 and the service life of the annular headband 1.

In one embodiment, the annular headband 1 comprises binding strips 5 wrapping edges of the annular headband 1. The binding strips 5 are respectively disposed along and wrap around the edges of the annular headband 1. The binding strips 5 wrap and sew raw edges of the sheet layers, which prevents fraying of the raw edges of the sheet layers and enhances overall firmness and delicacy of the annular headband 1.

In one embodiment, an internal width of each U-shaped pocket 13 is greater than a width of each pocket opening 14, so as to prevent each of the sound-producing bodies 6 from sliding out of a corresponding pocket opening 14 during a non-operational state. A spacious internal space defined by each U-shaped pocket 13 easily accommodates each of the sound-producing bodies 6, while the relatively narrow pocket opening 14 of each U-shaped pocket 13 exerts a certain degree of restraint on each of the sound-producing bodies 6. When the annular headband 1 is worn or shaken, each of the sound-producing bodies 6 is less likely to slide out because a size of each of the sound-producing bodies 6 is slightly larger than the width of each pocket opening 14, ensuring reliability during use and avoiding damage to the sound-producing bodies 6 due to accidental falling.

In one embodiment, an internal depth of each U-shaped pocket 13 is greater than a length of each of the sound-producing bodies 6, so as to facilitate the user to adjust a longitudinal position of each of the sound-producing bodies 6 within the corresponding one of the ear-covering segments 12 to accommodate different users. By sewing each U-shaped pocket to have the length greater than the length of each of the sound-producing bodies 6, space is reserved for a forward and backward movement of each of the sound-producing bodies 6 within the corresponding U-shaped pocket 13. Since positions of the auricles of different users vary slightly, a length design of each U-shaped pocket 13 allows the user to fine-tune the longitudinal position of each of the sound-producing bodies 6 within the corresponding one of the ear-covering segments 12 according to their own needs. In this way, the user is able to find an optimal wearing position where the sound-producing bodies respectively align with ear canals of the user, provide clear sound, and have less pressure, thereby enhancing the adaptability of the flexible sleeping headband-type speaker.

In one embodiment, a noise-muffling effect of a material of the inner layer 121 of each of the ear-covering segments 12 is less than a noise-muffling effect of a material of the outer layer of each of the ear-covering segments 12, so as to reduce attenuation of a volume of each of the sound-producing bodies 6. The outer layer 122 of each of the ear-covering segments 12 uses a high-density material with good sound insulation mainly for blocking noise from the outside environment. In contrast, the inner layer 121 of each of the ear-covering segments, which is directly adjacent to the corresponding ear, selects a relatively thin material with better sound permeability (such as specific cotton or knitted fabrics). The audio sound waves generated by each of the sound-producing bodies 6 experience less attenuation when propagating inward, allowing the user to obtain a clearer listening experience at a lower volume.

In one embodiment, the cushioning layers 2 are made of a fluffy cotton material. Each of the ear-covering segments 12 further comprises a middle layer 123 covering a corresponding one of the cushioning layers 2. Each middle layer 123 is disposed between the corresponding one of the cushioning layers 2 and a corresponding one of the sound-producing bodies 6. For each of the ear-covering segments 12, the middle layer 123 thereof, the corresponding one of the cotton product, and the inner layer 121 thereof are sequentially overlapped and sewn to form a closed interlayer, and a space between the outer layer thereof and the middle layer 123 thereof is sewn to form a non-closed interlayer. Each non-closed interlayer is defined as each U-shaped pocket 13.

The fluffy cotton material acts as a core cushioning substance and combines with the middle layer 123 and the inner layer 121 of each of the ear-covering segments 12 to form a firm cushioning pad. Each of the sound-producing bodies 6 is then placed in the corresponding U-shaped pocket 13 between each cushioning pad and the outer layer 122 of the corresponding one of the ear-covering segments 12. By covering each of the cushioning layers 2 with a corresponding middle layer 123, surface materials inside and outside the U-shaped pocket 13 are unified, which not only enhances integration of the annular headband but also prevents each cushioning pad from easily wearing out due to direct contact with each of the sound-producing bodies 6, thereby extending the service life of each cushioning pad.

In one embodiment, the adjustable segment 4 of the annular headband 1 is located in a position of the annular headband 1 corresponding to a back of the head of the user. The adjustable segment 4 is configured to adjust the perimeter of the annular headband 1. By adjusting the perimeter via the adjustable segment 4, an impact on structural and functional integrity of the eye-mask segment 11 and the ear-covering segments 12 on two sides is minimized.

In one embodiment, the adjustable segment 4 of the annular headband 1 is made of an elastic fabric. Two ends of the adjustable segment 4 are respectively sewn to tail portions of the ear-covering segments 12 away from the eye-mask segment 11 to form the annular headband 1. The elastic fabric relies on its own inherent elasticity to achieve automatic adjustment of the perimeter of the annular headband 1 to adapt to different head sizes, featuring a simple structure that is easy to process.

The present disclosure provides embodiments of the annular headband 1.

Embodiment 1

As shown in FIGS. 1-3 and 6-7, the adjustable segment 4 of the annular headband 1 is formed by two segments hooked via buckles. In this embodiment, the adjustable segment 4 comprises an adjusting strap 42 made of an elastic material and a tri-glide slide 43. One of the adjusting straps 42 is fixedly connected to one end of a first ear-covering segment 12. A hook 41 is disposed on a second end of the adjusting strap 42. A hanging ring 16 is disposed on one end of a second ear-covering segment 12. The hook 41 hooks on the hanging ring 16. The adjusting strap 42 has a fixed end and a movable end. The fixed end of the adjusting strap 42 is fixedly connected to one end of the first ear-covering segment 12, and the movable end of the adjusting strap 42 sequentially passes through two parallel ring holes of the tri-glide slide 43 and is fixedly connected to a middle portion of the tri-glide slide 43. In this way, a segment of the adjusting strap 42 between the tri-glide slide 43 and the movable end of the adjusting strap 42 enclose an adjusting loop with an adjustable perimeter. The hook 41 is slidably sleeved on the adjusting loop. By sliding the tri-glide slide 43, the perimeter of the adjusting loop is easily and continuously changed, thereby achieving adjustment of the length of the adjustable segment 4 to adapt to different head sizes and meet wearing requirements.

Embodiment 2

Figure 5:
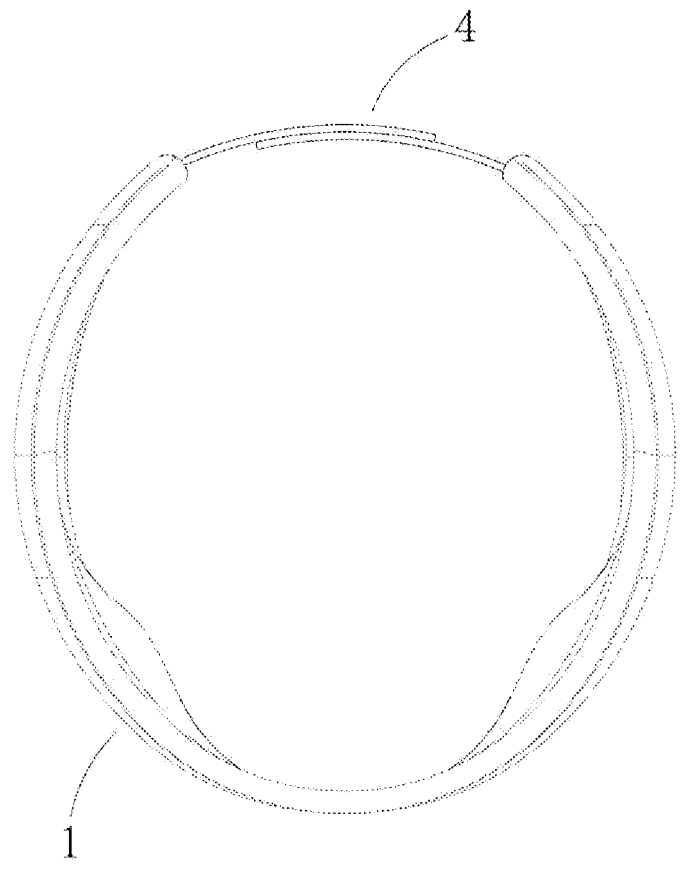
FIG. 5 is a top plan schematic diagram of the annular headband according to a second embodiment of the present disclosure.
Figure 6:
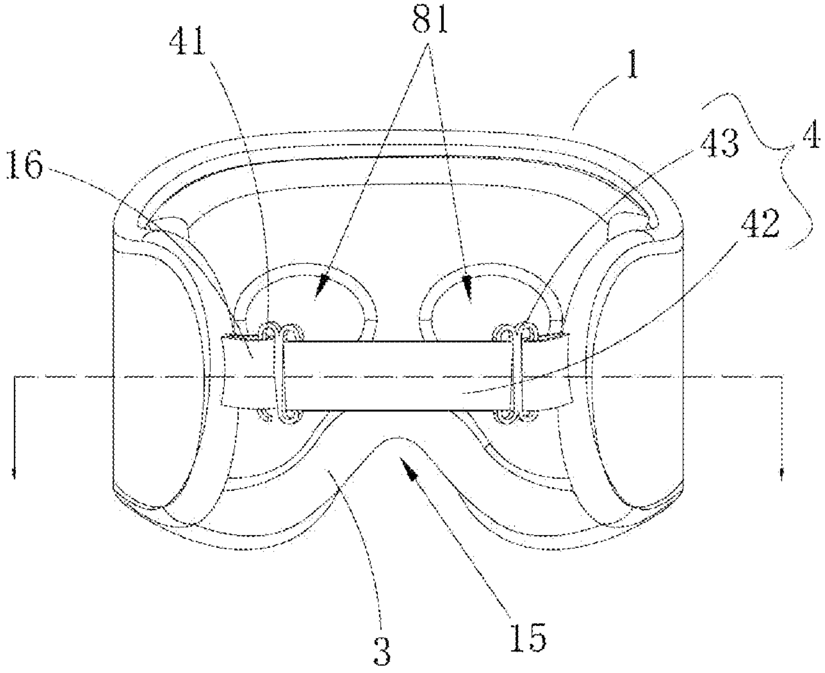
FIG. 6 is a rear side schematic diagram of the annular headband according to the first embodiment of the present disclosure, where the sound-producing bodies are accommodated in the annular headband.
Figure 7:
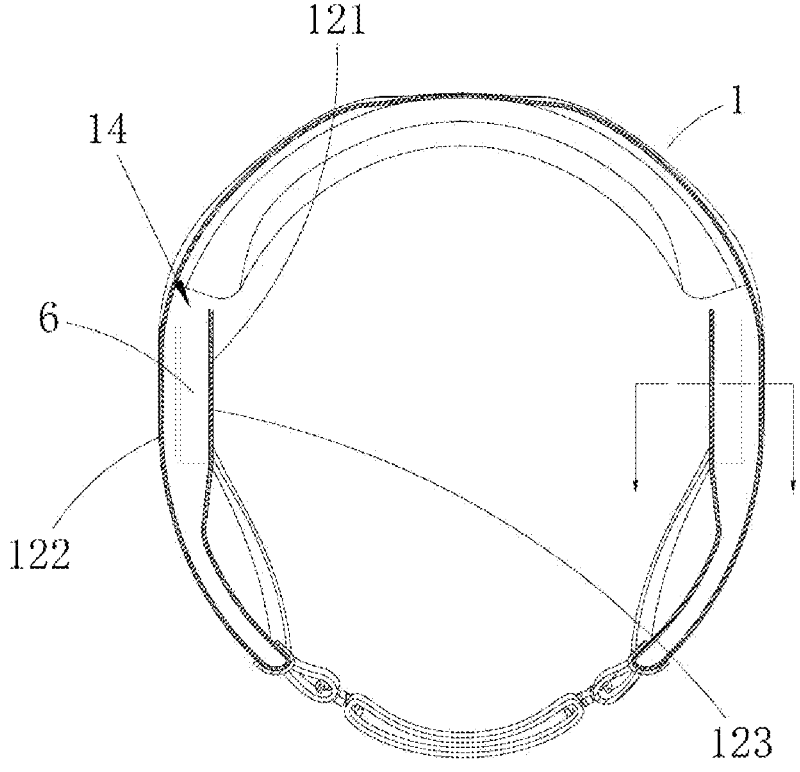
FIG. 7 is a cross-sectional schematic diagram of the annular headband shown in FIG. 6.
Figure 8:
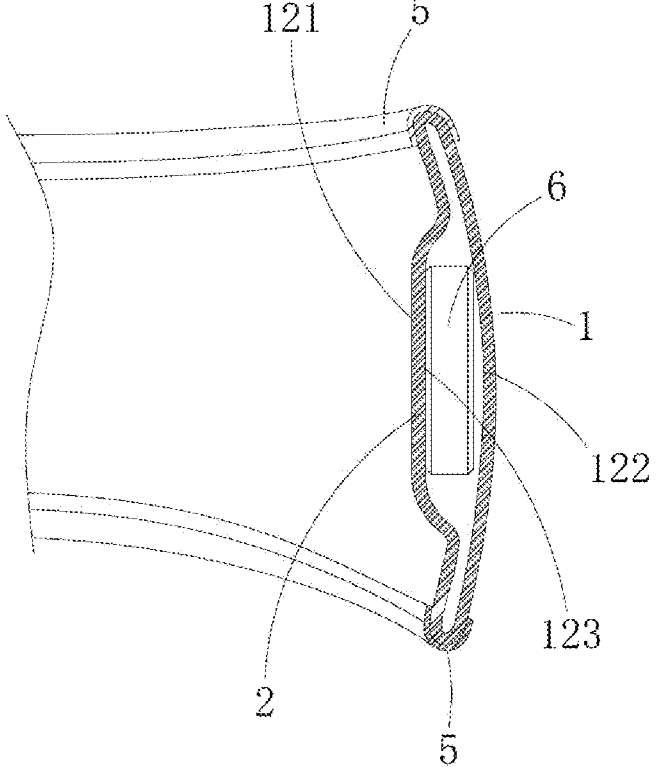
FIG. 8 is a partial cross-sectional schematic diagram of the annular headband shown in FIG. 7.
Figure 9:
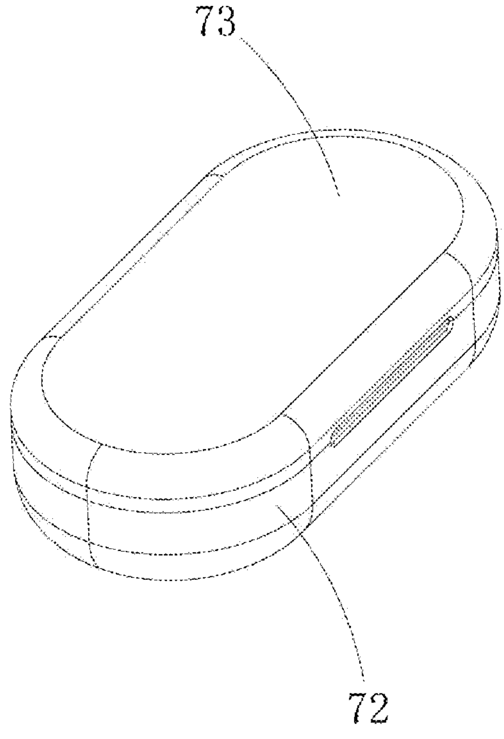
FIG. 9 is a perspective schematic diagram of a charging case of the present disclosure, where a flipping cover is closed.
Figure 10:
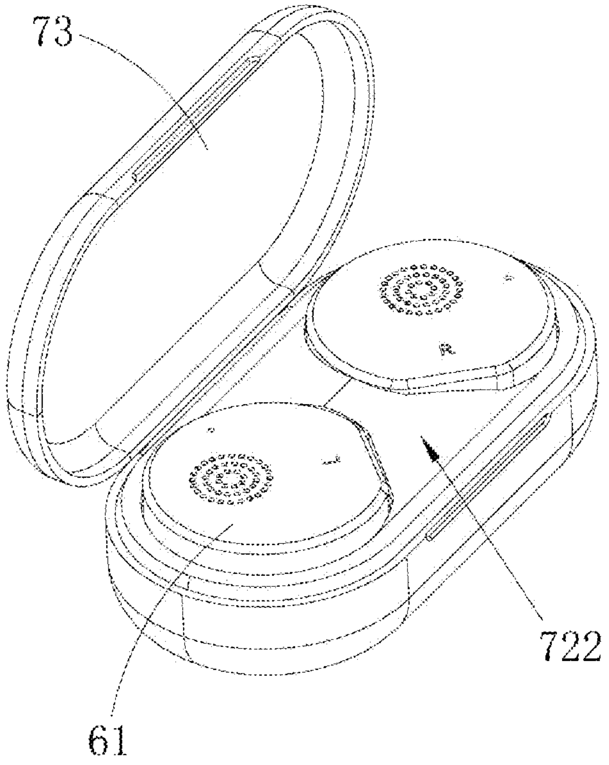
FIG. 10 is a perspective schematic diagram of the charging case of the present disclosure, where the flipping cover is opened.
Figure 11:
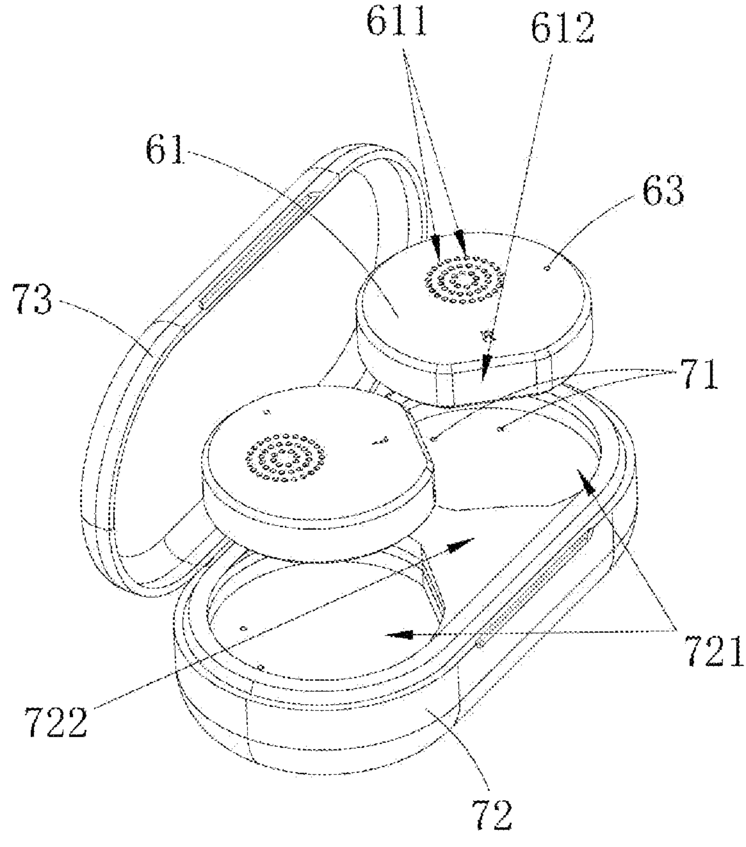
FIG. 11 is an exploded schematic diagram of the charging case and the sound-producing bodies of the present disclosure.

As shown in FIG. 5, in one embodiment, the adjustable segment 4 of the annular headband 1 is formed by two segments attached via hook-and-loop fasteners. Alternatively, the adjustable segment 4 is formed by two segments pressed via snap buttons (not shown in the drawings). Connecting parts, such as the hook-and-loop fasteners and the snap buttons, allow the user to perform manual multi-stage adjustment of the perimeter of the annular headband 1, thereby allowing the user to precisely control a wearing tightness of the annular headband 1 according to their own needs.

Embodiment 3

Figure 4:
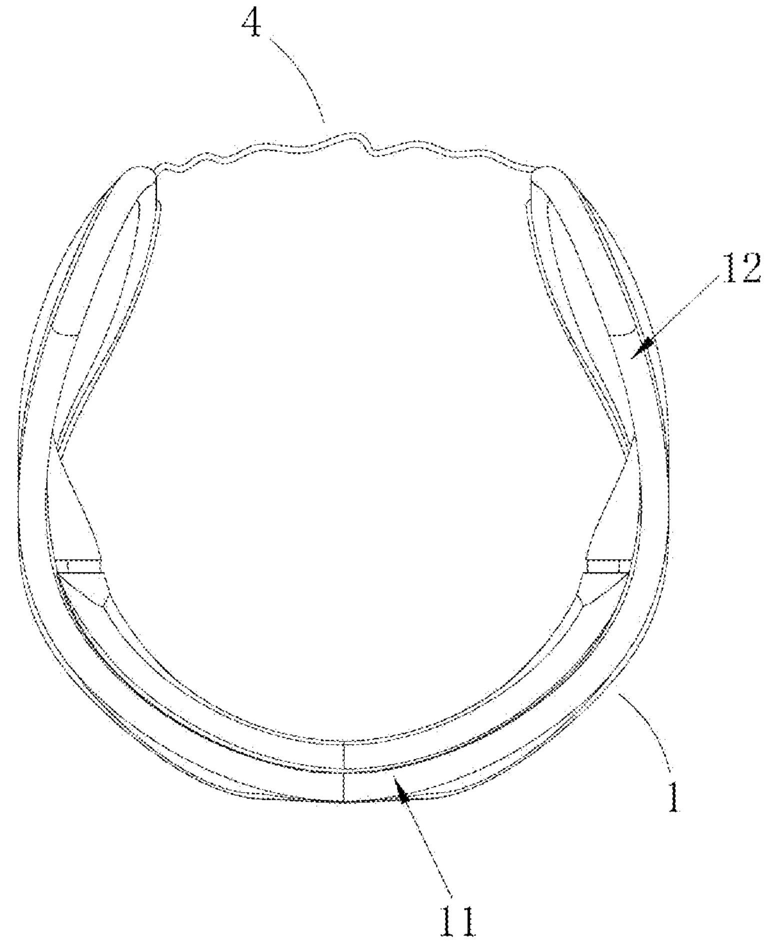
FIG. 4 is a top plan schematic diagram of the annular headband according to a third embodiment of the present disclosure.

As shown in FIG. 4, in one embodiment, two ends of the adjustable segment 4 are respectively sewn to the tail portions of the two ear-covering segments 12 away from the eye-mask segment 11 to form the complete annular headband 1, which is suitable for producing the flexible sleeping headband-type speaker of a standard size or a specific size (such as children's versions), featuring a simple, reliable structure and low cost.

In one embodiment, the width of the eye-mask segment 11 is greater than the width of each of the ear-covering segments 12. The width of each of the ear-covering segments 12 is greater than a width of the adjustable segment 4. The annular headband 1 features a stepwise decreasing width that is wider at a front portion thereof and narrower at a rear portion thereof. The eye-mask segment 11 corresponding to a forehead area has a maximum width to ensure sufficient light-blocking area. Each of the ear-covering segments 12 corresponding to the corresponding ear has a moderate width to accommodate the corresponding one of the sound-producing bodies 6 and provide noise-muffling while avoiding excessive bulkiness. The adjustable segment 4 corresponding to the back of the head has a minimum width to reduce a contact area with the head and the sensation of foreign objects, enhancing breathability and a lightweight wearing feel.

In one embodiment, a length of the eye-mask segment 11 distributed along the circumference of the annular headband 1 is less than a sum of lengths of the two ear-covering segments 12 and a length of the adjustable segment 4.

In one embodiment, in a packaging state of the flexible sleeping headband-type speaker, the eye-mask segment 11 is folded inward from a middle portion thereof to substantially wrap the ear-covering segments 12 and the adjustable segment 4 inside the eye-mask segment 11. An area of each pocket opening 14 facing away from the ear-covering segments 12 is configured as an inwardly-folded position. A middle portion of the adjustable segment 4 is configured as an outwardly-folded position. A packaging thickness of the flexible sleeping headband-type speaker is approximately twice a thickness of the eye-mask segment 11 plus a total thickness of the ear-covering segments 12.

In one embodiment, a cushioning lining 8 is fixedly laid on an inner wall of the eye-mask segment 11. Two recesses 81 are symmetrically disposed on the cushioning lining 8 along the circumference of the annular headband 1 for providing space for the eyes. The cushioning lining 8 with the recesses 81 is matched with a three-dimensional contour of the eye sockets, where the recesses 81 provide spaces for the eyeballs to prevent direct pressure on the eyeballs, while surrounding areas of the recesses fit and support the orbital bones, uniformly dispersing pressure, thereby reducing pressure sensation while blocking light and enhancing wearing comfort.

In one embodiment, a nose-bridge notch 15 is formed at a middle lower end of the eye-mask segment 11, and a contour of the nose-bridge notch 15 is adapted to a nose to provide space for the nose. A light-blocking flap 3 is disposed on the inner side of the eye-mask segment 11 along an edge of the nose-bridge notch 15. The light-blocking flap 3 is configured to fit the bridge and nostrils of the nose to prevent light from entering from two sides of the nose. The nose-bridge notch 15 itself avoids pressure from the annular headband on the nose, while the light-blocking flap 3 naturally fits two sides of the bridge of the nose of the user upon wearing, filling a gap between the nose and eye-mask segment, thereby effectively reducing light leakage from a nasal sides and ensuring a light-blocking effect of the annular headband.

The present disclosure further provides a flexible sleeping headband-type speaker. The flexible sleeping headband-type speaker comprises an annular headband 1, two sound-producing bodies 6, and a control system. The annular headband 1 comprises an adjustable segment 4, an eye-mask segment 11, and ear-covering segments 12. The adjustable segment 4 is disposed along a circumference of the annular headband 1 to adjust a perimeter of the annular headband 1, so as to adapt to different head sizes while maintaining a gentle tension. The eye-mask segment 11 is configured to cover an eye area. The ear-covering segments 12 are symmetrically disposed and are respectively configured to cover a left ear and a right ear. Each of the ear-covering segments 12 features at least a triple-layer consisting of an inner layer 121, and an outer layer, and a cushioning layer disposed between the inner layer 121 and the outer layer. Each of the sound-producing bodies 6 is a flat structure. The sound-producing bodies 6 are configured to receive audio information and convert the audio information into audio sound waves. Each of the sound-producing bodies 6 is positioned between the cushioning layer and the outer layer of a corresponding one of the ear-covering segments 12. An acoustic axis of each of the sound-producing bodies 6 is roughly perpendicular to the corresponding one of the ear-covering segments 12. A sound emitted by each of the sound-producing bodies 6 is capable of passing through the cushioning layer and the inner layer 121 of the corresponding one of the ear-covering segments 12 to reach a corresponding ear.

The control system is configured to control the sound-producing bodies 6 and is disposed on a middle portion of the eye-mask segment 11. A circuit board of the control system is fixed in an interlayer of the eye-mask segment 11. A control panel of the control system is fixed on an outer surface of the eye-mask segment 11, and connecting wires connecting the control system and the sound-producing bodies 6 pass through an interlayer of the annular headband 1.

In one embodiment, each cushioning layer is made of a sound-permeable material to disperse and alleviate localized pressure that each of the sound-producing bodies 6 exerts on a corresponding ear. For each of the ear-covering segments 12, the cushioning layer thereof and the inner layer 121 thereof are sewn to form a closed interlayer, and the cushioning layer thereof and the outer layer thereof are sewn to form a U-shaped pocket 13 configured to accommodate a corresponding one of the sound-producing bodies 6.

The present disclosure further provides a flexible sleeping headband-type speaker. The flexible sleeping headband-type speaker comprises an annular headband 1, two sound-producing bodies 6, and a charging case. The annular headband 1 comprises an adjustable segment 4, an eye-mask segment 11, and ear-covering segments 12. The adjustable segment 4 is disposed along a circumference of the annular headband 1 to adjust a perimeter of the annular headband 1, so as to adapt to different head sizes while maintaining a gentle tension. The eye-mask segment 11 is configured to cover an eye area.

The ear-covering segments 12 are symmetrically disposed and are respectively configured to cover a left ear and a right ear. Each of the ear-covering segments 12 features at least a triple-layer consisting of an inner layer 121, and an outer layer, and a cushioning layer disposed between the inner layer 121 and the outer layer. Each cushioning layer is made of a sound-permeable material to disperse and alleviate localized pressure that each of the sound-producing bodies 6 exerts on a corresponding ear. Each of the sound-producing bodies 6 is a flat structure. Each of the sound-producing bodies 6 is positioned between the cushioning layer and the outer layer of a corresponding one of the ear-covering segments 12. A sound emitted by each of the sound-producing bodies 6 is capable of passing through the cushioning layer and the inner layer 121 of the corresponding one of the covering segments to reach a corresponding ear. The sound-producing bodies 6 are allowed to be charged in the charging case after being taken out of the annular headband 1.

In one embodiment, each of the sound-producing bodies 6 comprises a housing 61, a speaker, a music circuit board, a music battery, and a power receiving component. the embodiment takes one of the sound-producing bodies 6 as an example for further illustration.

The housing 61 features a flat and hollow structure. The speaker, the music circuit board, the music battery, and the power receiving component are disposed inside the housing 61. Sound holes 611 are formed on a sidewall of the housing 61 perpendicular to a thickness direction thereof. The speaker faces the sound holes 611. The music battery supplies power to the speaker via the music circuit board, and the power receiving component is electrically connected to the music circuit board. When the user uses the flexible sleeping headband-type speaker, the music battery supplies power to the entire circuit, the music circuit board drives the speaker to vibrate, and sound is transmitted outward through the sound holes 611.

In one embodiment, an indicator light 63 electrically connected to the music circuit board is further disposed on the sidewall of the housing 61 where the sound holes 611 are formed. When the one of the sound-producing bodies 6 is in a working state, such as power-on, Bluetooth pairing, or low battery, the indicator light 63 emits light of a specific color to notify the user. In this way, the user is allowed to directly understand a current working state or remaining power of the one of the sound-producing bodies 6, thereby enhancing the use convenience.

In one embodiment, a cross-section of the housing 61 is circular, and such a streamlined contour without sharp corners provides a smoother tactile feel and fluent operation when the user places the one of the sound-producing bodies 6 into or removes the one of the sound-producing bodies 6 from the corresponding U-shaped pocket 13. There is no sharp corner that may snag or wear the fabric material, thereby protecting the flexible sleeping headband-type speaker while enhancing safety during handling and operation.

In one embodiment, the flexible sleeping headband-type speaker further comprises a charger. The charger comprises power output components 71. Each power receiving component is electrically connected to a corresponding one of the power output components 71 to charge a corresponding music battery. When the sound-producing bodies 6 are fixedly disposed within the annular headband 1, charging ports are respectively formed on two sides of the annular headband 1. Each of the charging ports is connected to the power receiving component. Each of the power output components 71 of the charging case is electrically connected to each power receiving component through a corresponding charging port to charge the corresponding music battery.

In one embodiment, the charger comprises a charging case 72, as well as a charging circuit board and a charging battery built into the charging case 72. Two charging cavities 721 for placing the sound-producing bodies 6 are respectively formed at a top portion of the charging case 72. First contact points electrically connected to a corresponding charging battery via a corresponding charging circuit board are disposed on an inner wall of each of the charging cavities 721. The first contact points are defined as the power output components 71. Second contact points are disposed on a sidewall of each housing 61 opposite to corresponding sound holes 611. The second contact points on each housing are defined as each power receiving component. When the sound-producing bodies 6 are placed within the charging cavities 721, the second contact points of each of the sound-producing bodies 6 are connected to corresponding first contact points, and each charging battery charges the corresponding music battery. When the user places the sound-producing bodies 6 into the charging cavities 721, the second contacts on the back of the sound-producing bodies 6 automatically attract and connect to the first contacts in the cavities (the attraction method is prior art and is not elaborated in this embodiment). At this time, the charging battery built into the charging case 72 starts to charge the music batteries within the sound-producing bodies 6. The charging case 72 is not only a charging device but also a container for storage and protection, which can safely replenish power for the two sound-producing bodies 6 simultaneously and extend their overall standby time.

In one embodiment, a flat wall 612 parallel to an axial direction is disposed at one end of each housing 61. A contour of each of the charging cavities 721 is matched with each housing 61, so that each housing 61 is aligned via the flat wall 612 thereof and laid flat within the corresponding one of the charging cavity 721. In this way, each of the sound-producing bodies 6 is only allowed to be stably placed into the corresponding one of the charging cavities 721 in a specific direction (where the flat wall 612 thereof aligns with a corresponding edge of the corresponding one of the charging cavities 721). This "poka-yoke" (error-proofing) design forces the user to place the sound-producing bodies 6 in the only correct posture, ensuring that the second contact points on the rear side of each of the sound-producing bodies 6 always accurately align with the first contact points in the corresponding one of the charging cavities 721, thereby avoiding poor contact or charging failure caused by incorrect placement directions and enhancing charging reliability.

In one embodiment, a charging interface is disposed on one side of the charging case 72, and the charging interface is electrically connected to the charging battery via the charging circuit board.

In one embodiment, the charging interface is a Type-C interface. The user is allowed to use the same cable for charging mobile phones, tablets, and other devices to charge the charging case 72, eliminating a need to carry a dedicated charging cable and enhancing convenience during travel and device versatility.

In one embodiment, a flipping cover 73 is hinged to one side of the charging case 72. The flipping cover 73 is configured to cover the charging cavities 721, thereby effectively preventing dust, hair, and other foreign objects from falling into the charging cavities 721 and contaminating metal contacts (i.e., first contact points and second contact points), while preventing the sound-producing bodies 6 placed inside from easily falling out due to accidental collision or movement.

In one embodiment, two charging cavities 721 are symmetrically disposed at the top portion of the charging case 72. A finger groove 722 is formed at the top portion of the charging case 72 between the two charging cavities 721 to connect the two charging cavities 721. The finger groove 722 provides space for the fingers of the user to apply force, enabling the user to easily take out the sound-producing bodies 6 embedded in the two charging cavities 721 and reducing the difficulty of removal.

In one embodiment, the charging case 72 has a built-in display device, and at least a front sidewall of the charging case 72 is made of a transparent or semi-transparent material for displaying characters shown by the built-in display device.

In one embodiment, the built-in display device comprises a display board with hollow symbols (such as battery icons or percentage numbers) and a light board. The display board is disposed between the light board and the front sidewall of the charging case 72. At least one light-transmitting symbol is disposed on the display board. The light board is electrically connected to the charging circuit board, and at least one LED bead is disposed on the light board corresponding to the light-transmitting symbol. When the charging case 72 works, the charging circuit board controls the corresponding LED beads to light up based on a power level. The light passes through specific symbols on the display board to show clear characters on the display board. In this way, precise and eye-catching state information display in a low-cost, low-power-consumption manner is achieved. For example, numbers representing "25%", "50%", "75%", or "100%" power level may be lit up, allowing the user to obtain precise battery information.

Obviously, the embodiments described above are merely some rather than all of the embodiments of the present disclosure, and the accompanying drawings show optional embodiments of the present disclosure, but do not limit the patent scope of the present disclosure. The present disclosure may be implemented in many different forms, and the purpose of providing these embodiments is to make the understanding of the present disclosure more thorough and comprehensive. Although the present disclosure has been described in detail with reference to the foregoing embodiments, for those skilled in the art, the technical solutions described in the foregoing specific embodiments may still be modified, or some of the technical features may be equivalently replaced. Any equivalent structure made by using the content of the specification and the accompanying drawings of the present disclosure is directly or indirectly applied to other related technical fields, which are all within the scope of protection of the present disclosure.

What is claimed is:

1. A flexible sleeping headband-type speaker, comprising: an annular headband; two sound-producing bodies; and cushioning layers; wherein the annular headband comprises an adjustable segment, an eye-mask segment, and ear-covering segments; wherein the adjustable segment is disposed along a circumference of the annular headband to adjust a perimeter of the annular headband, so as to adapt to different head sizes while maintaining a gentle tension; wherein the eye-mask segment is configured to cover an eye area, and a width of the eye-mask is sufficient to provide a light-blocking function; wherein the ear-covering segments are symmetrically disposed and are respectively configured to cover a left ear and a right ear, a width of each of the ear-covering segments is sufficient to provide a noise-muffling effect, and each of the ear-covering segments features at least a dual-layer structure consisting of an inner layer and an outer layer; wherein each of the sound-producing bodies is a flat structure, the sound-producing bodies are configured to receive audio information and convert the audio information into audio sound waves, each of the sound-producing bodies is positioned between the inner layer and the outer layer of a corresponding one of the ear-covering segments, and an acoustic axis of each of the sound-producing bodies is roughly perpendicular tithe corresponding one of the ear-covering segments and faces inward; wherein the cushioning layers are made of a sound-permeable material, each of the cushioning layers is positioned between the inner layer of a corresponding one of the ear-covering segments and a corresponding one of the sound-producing bodies, the cushioning layers are configured to disperse and alleviate any localized pressure that the sound-producing bodies exert on the left ear and the right ear; wherein each of the cushioning layers and the outer layer of the corresponding one of the ear-covering segments are sewn to form a U-shaped pocket that is horizontally disposed, each U-shaped pocket is configured to accommodate a corresponding one of the sound-producing bodies; wherein a sound emitted by each of the sound-producing bodies is capable of passing through a corresponding one of the cushioning layer and the inner layer of the corresponding one of the ear-covering segments to reach a corresponding ear; wherein each of the cushioning layers and the inner layer of the corresponding one of the ear-covering segments are sewn together to form a closed interlayer, so that each of the sound-producing bodies is prevented from being mistakenly placed between each of the cushioning layers and the inner layer of the corresponding one of the ear-covering segments; wherein a pocket opening of each U-shaped pocket is located between each U-shaped pocket and the eye-mask segment, so that each of the sound-producing bodies is allowed to be placed into a corresponding U-shaped pocket from front to rear; wherein a length of the eye-mask segment distributed along the circumference of the annular headband is less than a sum of lengths of the two ear-covering segments and a length of the adjustable segment; and wherein in a packaging state of the flexible sleeping headband-type speaker, the eye-mask segment is folded inward from a middle portion thereof to substantially wrap the ear-covering segments and the adjustable segment inside the eye-mask segment; an area of each pocket opening facing away from the ear-covering segments is configured as an inwardly-folded position; a middle portion of the adjustable segment is configured as an outwardly-folded position; and a packaging thickness of the flexible sleeping headband-type speaker is approximately twice a thickness of the eye-mask segment plus a total thickness of the ear-covering segments.

2. The flexible sleeping headband-type speaker according to claim 1, wherein the pocket opening of each U-shaped pocket is disposed on an inner side of the annular headband to avoid affecting an appearance of the annular headband.

3. The flexible sleeping headband-type speaker according to claim 2, wherein in a transition area between each of the ear-covering segments and the eye-mask segment, the inner layer of each of the ear-covering segments is sewn onto an inner layer of the eye-mask segment, and an upper part of a sewn line thereof defines a pick-and-place gap having a size not less than a width of each of the sound-producing bodies, so as to form each pocket opening.

4. The flexible sleeping headband-type speaker according to claim 3, wherein the pick-and-place gap of each pocket opening is perpendicular to the circumference of the annular headband, so that an opening direction of the pocket opening faces toward the eye-mask segment along the circumference of the annular headband.

5. The flexible sleeping headband-type speaker according to claim 4, wherein an edge of the pocket opening of the inner layer of each of the ear-covering segments is sewn with a pocket binding; each pocket binding is inwardly-folded;

wherein each pocket binding is tubular and hollow, and a reinforcing rib is wrapped by each pocket binding to prevent excessive deformation of each pocket opening, so as to reduce pulling of each pocket opening when placing or removing a corresponding one of the sound-producing bodies and avoid premature damage to each U-shaped pocket.

6. The flexible sleeping headband-type speaker according to claim 1, wherein an internal width of each U-shaped pocket is greater than a width of each pocket opening, so as to prevent each of the sound-producing bodies from sliding out of a corresponding pocket opening during a non-operational state.

7. The flexible sleeping headband-type speaker according to claim 1, wherein an internal depth of each U-shaped pocket is greater than a length of each of the sound-producing bodies, so as to facilitate a user to adjust a longitudinal position of each of the sound-producing bodies within the corresponding one of the ear-covering segments to accommodate different users.

8. The flexible sleeping headband-type speaker according to claim 1, wherein a noise-muffling effect of a material of the inner layer of each of the ear-covering segments is less than a noise-muffling effect of a material of the outer layer of each of the ear-covering segments, so as to reduce attenuation of a volume of each of the sound-producing bodies.

9. The flexible sleeping headband-type speaker according to claim 1, wherein the cushioning layers are made of a fluffy cotton material, each of the ear-covering segments further comprises a middle layer covering a corresponding one of the cushioning layers, and each middle layer is disposed between the corresponding one of the cushioning layers and a corresponding one of the sound-producing bodies; wherein for each of the ear-covering segments, the middle layer thereof, the corresponding one of the cotton product, and the inner layer thereof are sequentially overlapped and sewn to form a closed interlayer, and a space between the outer layer thereof and the middle layer thereof is sewn to form a non-closed interlayer; wherein each non-closed interlayer is defined as each U-shaped pocket.

10. The flexible sleeping headband-type speaker according to claim 1, wherein two ends of the adjustable segment are respectively sewn to tail portions of the ear-covering segments away from the eye-mask segment to form the annular headband, so as to adjust the perimeter of the annular headband.

11. The flexible sleeping headband-type speaker according to claim 10, wherein the adjustable segment of the annular headband is made of an elastic fabric; or the adjustable segment of the annular headband is formed by two segments attached via hook-and-loop fasteners; or the adjustable segment of the annular headband is formed by two segments hooked via buckles; or the adjustable segment of the annular headband is formed by two segments pressed via snap buttons.

12. The flexible sleeping headband-type speaker according to claim 10, wherein the width of the eye-mask segment is greater than the width of each of the ear-covering segments; the width of each of the ear-covering segments is greater than a width of the adjustable segment; and the annular headband features a stepwise decreasing width that is wider at a front portion thereof and narrower at a rear portion thereof.

13. A flexible sleeping headband-type speaker, comprising: an annular headband; two sound-producing bodies; and a control system; wherein the annular headband comprises an adjustable segment, an eye-mask segment, and ear-covering segments; wherein the adjustable segment is disposed along a circumference of the annular headband to adjust a perimeter of the annular headband, so as to adapt to different head sizes while maintaining a gentle tension; wherein the eye-mask segment is configured to cover an eye area; wherein the ear-covering segments are symmetrically disposed and are respectively configured to cover a left ear and a right ear, and each of the ear-covering segments features at least a triple-layer consisting of an inner layer, and an outer layer, and a cushioning layer disposed between the inner layer and the outer layer; wherein each of the sound-producing bodies is a flat structure, the sound-producing bodies are configured to receive audio information and convert the audio information into audio sound waves, each of the sound-producing bodies is positioned between the cushioning layer and the outer layer of a corresponding one of the ear-covering segments, and an acoustic axis of each of the sound-producing bodies is roughly perpendicular to the corresponding one of the ear-covering segments; wherein a sound emitted by each of the sound-producing bodies is capable of passing through the cushioning layer and the inner layer of the corresponding one of the ear-covering segments to reach a corresponding ear; wherein the control system is configured to control the sound-producing bodies and is disposed on a middle portion of the eye-mask segment, a circuit board of the control system is fixed in an interlayer of the eye-mask segment, a control panel of the control system is fixed on an outer surface of the eye-mask segment, connecting wires connecting the control system and the sound-producing bodies pass through an interlayer of the annular headband; wherein the cushioning layers are made of a sound-permeable material, each of the cushioning layers is positioned between the inner layer of a corresponding one of the ear-covering segments and a corresponding one of the sound-producing bodies, the cushioning layers are configured to disperse and alleviate any localized pressure that the sound-producing bodies exert on the left ear and the right ear; wherein each of the cushioning layers and the outer layer of the corresponding one of the ear-covering segments are sewn to form a U-shaped pocket that is horizontally disposed, each U-shaped pocket is configured to accommodate a corresponding one of the sound-producing bodies; wherein a sound emitted by each of the sound-producing bodies is capable of passing through a corresponding one of the cushioning layer and the inner layer of the corresponding one of the ear-covering segments to reach a corresponding ear; wherein each of the cushioning layers and the inner layer of the corresponding one of the ear-covering segments are sewn together to form a closed interlayer, so that each of the sound-producing bodies is prevented from being mistakenly placed between each of the cushioning layers and the inner layer of the corresponding one of the ear-covering segments; wherein a pocket opening of each U-shaped pocket is located between each U-shaped pocket and the eye-mask segment, so that each of the sound-producing bodies is allowed to be placed into a corresponding U-shaped pocket from front to rear; wherein a length of the eye-mask segment distributed along the circumference of the annular headband is less than a sum of lengths of the two ear-covering segments and a length of the adjustable segment; and wherein in a packaging state of the flexible sleeping headband-type speaker, the eye-mask segment is folded inward from a middle portion thereof to substantially wrapthe ear-covering segments and the adjustable segment inside the eye-mask segment; an area of each pocket opening facing away from the ear-covering segments is configured as an inwardly-folded position; a middle portion of the adjustable segment is configured as an outwardly-folded position; and a packaging thickness of the flexible sleeping headband-type speaker is approximately twice a thickness of the eye-mask segment plus a total thickness of the ear-covering segments.

14. A flexible sleeping headband-type speaker, comprising: an annular headband; two sound-producing bodies; and a charging case; wherein the annular headband comprises an adjustable segment, an eye-mask segment, and ear-covering segments; wherein the adjustable segment is disposed along a circumference of the annular headband to adjust a perimeter of the annular headband, so as to adapt to different head sizes while maintaining a gentle tension; wherein the eye-mask segment is configured to cover an eye area; wherein the ear-covering segments are symmetrically disposed and are respectively configured to cover a left ear and a right ear, and each of the ear-covering segments features at least a triple-layer consisting of an inner layer, and an outer layer, and a cushioning layer disposed between the inner layer and the outer layer; wherein each cushioning layer is made of a sound-permeable material to disperse and alleviate localized pressure that each of the sound-producing bodies exerts on a corresponding ear; wherein each of the sound-producing bodies is a flat structure, each of the sound-producing bodies is positioned between the cushioning layer and the outer layer of a corresponding one of the ear-covering segments, and a sound emitted by each of the sound-producing bodies is capable of passing through the cushioning layer and the inner layer of the corresponding one of the covering segments to reach a corresponding ear; wherein the sound-producing bodies are allowed to be charged in the charging case after being taken out of the annular headband; wherein each of the cushioning layers and the outer layer of the corresponding one of the ear-covering segments are sewn to form a U-shaped pocket that is horizontally disposed, each U-shaped pocket is configured to accommodate a corresponding one of the sound-producing bodies; wherein a sound emitted by each of the sound-producing bodies is capable of passing through a corresponding one of the cushioning layer and the inner layer of the corresponding one of the ear-covering segments to reach a corresponding ear; wherein each of the cushioning layers and the inner layer of the corresponding one of the ear-covering segments are sewn together to form a closed interlayer, so that each of the sound-producing bodies is prevented from being mistakenly placed between each of the cushioning layers and the inner layer of the corresponding one of the ear-covering segments; wherein a pocket opening of each U-shaped pocket is located between each U-shaped pocket and the eye-mask segment, so that each of the sound-producing bodies is allowed to be placed into a corresponding U-shaped pocket from front to rear; wherein a length of the eye-mask segment distributed along the circumference of the annular headband is less than a sum of lengths of the two ear-covering segments and a length of the adjustable segment; and wherein in a packaging state of the flexible sleeping headband-type speaker, the eye-mask segment is folded inward from a middle portion thereof to substantially wrapthe ear-covering segments and the adjustable segment inside the eye-mask segment; an area of each pocket opening facing away from the ear-covering segments is configured as an inwardly-folded position; a middle portion of the adjustable segment is configured as an outwardly-folded position; and a packaging thickness of the flexible sleeping headband-type speaker is approximately twice a thickness of the eye-mask segment plus a total thickness of the ear-covering segments.

* * * * *